US00RE46453E

(19) United States
(12) Reissued Patent
Sung et al.

(10) Patent Number: US RE46,453 E
(45) Date of Reissued Patent: Jun. 27, 2017

(54) COMPOSITIONS COMPRISING HPV POLYPEPTIDES AND IMMUNOENHANCEMENT PEPTIDES FOR THE TREATMENT AND PREVENTION OF CERVICAL CANCER

(71) Applicants: Postech Foundation, Pohang-Si (KR); Genexine, Inc., Seoul (KR)

(72) Inventors: Young Chul Sung, Pohang-si (KR); Hyun Tak Jin, Pohang-si (KR); Sang Hwan Seo, Pohang-si (KR); Sang Hoon Park, Anyang-si (KR); Je-In Youn, Chungcheongbuk-do (KR)

(73) Assignees: POSTECH FOUNDATION, Pohang-Si (KR); GENEXINE, INC., Seoul (KR)

(21) Appl. No.: 14/631,092

(22) Filed: Feb. 25, 2015

Related U.S. Patent Documents

Reissue of:
(64) Patent No.: 8,137,674
Issued: Mar. 20, 2012
Appl. No.: 12/297,407
PCT Filed: Apr. 19, 2006
PCT No.: PCT/KR2006/001448
§ 371 (c)(1),
(2) Date: Mar. 12, 2009
PCT Pub. No.: WO2007/119896
PCT Pub. Date: Oct. 25, 2007

(51) Int. Cl.

| | |
|---|---|
| ***A61K 39/00*** | (2006.01) |
| ***C07K 14/005*** | (2006.01) |
| ***C07K 14/475*** | (2006.01) |
| ***C07K 14/705*** | (2006.01) |
| ***C12N 7/00*** | (2006.01) |
| ***A61K 39/12*** | (2006.01) |

(52) U.S. Cl.
CPC ..... *C07K 14/005* (2013.01); *A61K 39/12* (2013.01); *C07K 14/475* (2013.01); *C07K 14/70575* (2013.01); *C12N 7/00* (2013.01); *A61K 2039/53* (2013.01); *A61K 2039/585* (2013.01); *C07K 2319/00* (2013.01); *C07K 2319/02* (2013.01); *C07K 2319/33* (2013.01); *C12N 2710/20022* (2013.01); *C12N 2710/20023* (2013.01); *C12N 2710/20034* (2013.01)

(58) Field of Classification Search
CPC ..... C07K 14/005; C07K 14/70575; C07K 14/475; A61K 39/12; C12N 7/00
See application file for complete search history.

(56) References Cited

U.S. PATENT DOCUMENTS

2004/0110925 A1 6/2004 Hu et al.
2007/0014810 A1* 1/2007 Baker et al. ..... 424/186.1

OTHER PUBLICATIONS

Lasaro, M. O. et al. "Anti-tumor DNA vaccines based on the expression of human papillomavirus-16 E6/E7 oncoproteins genetically fused with the glycoprotein D from herpes simplex virus-1" Microbes Infect., Dec. 2005, vol. 7, No. 15, pp. 1541-1550.
Hill, S. C. et al. "Avtivation of CD40 in cervical carcinoma cells facilitates CTL responses and augments chemotherapy-induced apoptosis" J. Immunol., Jan. 2005, vol. 174, No. 1, pp. 41-50.
Le Roux, L. G. et al. "Nuclear entry of high-risk human papillomavirus type 16 E6 oncoprotein occurs via several pathways" J. Virol., Feb. 2003, vol. 77, No. 4, pp. 2330-2337.
Hung et al., "Enhancement of DNA Vaccine Potency by Linkage of Antigen Gene to a Gene Encoding the Extracellular Domain of Fms-like Tyrosine Kinase 3-Ligand" Cancer Research, 2001, vol. 61, pp. 1080-1088.
International Search Report prepared by the Korean Intellectual Property Office on Jan. 12, 2007 for International Application No. PCT/KR2006/001448; Applicants, Postech Foundation and Genexine Co., Ltd.

* cited by examiner

*Primary Examiner* — Johnny F Railey
(74) *Attorney, Agent, or Firm* — Lathrop & Gage LLP

(57) ABSTRACT

The present invention relates to a fusion protein comprising a fusion polypeptide of E6 and E7 of a human papilloma virus, a signal peptide for secreting the polypeptide out of the cell, and an immune enhancing peptide for a subject; a polynucleotide encoding the fusion protein; and a vector containing the polynucleotide. The present invention further relates to a pharmaceutical composition comprising the fusion protein or the vector; and a method for treating a disease caused by a human papilloma virus using the pharmaceutical composition.

4 Claims, 3 Drawing Sheets

COMPOSITIONS COMPRISING HPV POLYPEPTIDES AND IMMUNOENHANCEMENT PEPTIDES FOR THE TREATMENT AND PREVENTION OF CERVICAL CANCER

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATIONS

This application is a *reissue application of U.S. Ser. No. 12/297,407, filed Mar. 12, 2009, now U.S. Pat. No. 8,137,674, entitled "Compositions comprising HPV polypeptides and immunoenhancement peptides for the treatment and prevention of cervical cancer," which is in turn a* national stage application under 35 U.S.C. 371 of PCT Application No. PCT/KR2006/001448 having an international filing date of Apr. 19, 2006, which designated the U.S., the entire disclosure of which is hereby incorporated herein by reference.

TECHNICAL FIELD

The present invention relates to a fusion protein comprising a fusion polypeptide of E6 and E7 of a human papilloma virus (HPV), a signal peptide for secreting the polypeptide out of the cell, and an immune enhancing peptide for a subject; a polynucleotide encoding the fusion protein; a vector containing the polynucleotide; a pharmaceutical composition comprising the fusion protein or the vector; and a method for treating a disease caused by a human papilloma virus using the pharmaceutical composition.

*SEQUENCE STATEMENT*

*Incorporated by reference herein in its entirety is the Sequence Listing entitled "Sequence Listing ST25," created Feb. 23, 2015, size of 22 kB.*

BACKGROUND ART

Cervical cancer has become the second leading cause of death of cancers, causing 250,000 deaths worldwide annually. Cervical cancer has been known to be mostly caused by a human papilloma virus (HPV) infection (zur Hausen, H et al. Biochem Biophys Acta 1996, 1288; F55-F78). Among hundreds of types of HPVs, HPV16 is known as the leading cause of cervical cancer (Mark H et al. J Natl Cancer Inst 1993, 85; 958-964). Among the HPV proteins, E6 and E7 proteins play critical roles in the occurrence of cervical cancer as oncogenes, and it has been reported that they are the major proteins which are expressed in about 99% of the tumors caused by HPVs. As a result, E6 and E7 proteins have become a major target antigen in the preparation of a vaccine to treat and prevent the cervical cancer (von Knebel Doeberitz et al. Int. J. Cancer 1992, 51; 831-834). E6 prevents apoptosis of the cells by inducing decomposition of a tumor-inhibiting protein p53, and E7 binds to a retinoblastoma protein (Rb) which is a cellular tumor suppressor, to inactivate the protein, and then to induce the cells to enter an S phase in the cell cycle (Cobrinik et al., Trends Biochem Sci 1992, 17:312-5).

A clinical test using a composition expressing a nucleic acid base sequence which expresses HPV16 E6 and E7 proteins at the same time was performed in order to treat the cervical cancer, but its therapeutic effect was not significant (Garcia F et al. Obstet Gynecol 2004, 103; 317-326). Further, International Patent Publication WO 2004/030636 discloses a fusion polypeptide comprising E6 and E7, wherein the E6 is at an amino terminal or a carboxyl terminal, and a polynucleotide encoding the fusion polypeptide. However, the polypeptide as disclosed in this document still has limitation in treating the cervical cancer caused by HPV.

Therefore, the present inventors have found that a fusion protein comprising an E6/E7 fusion polypeptide of HPV bonded with a secretory peptide and an immune enhancing peptide improves immune responses, and is effective in treatment and prevention of the tumors caused by HPV, thereby completing the present invention.

DISCLOSURE

Technical Solution

It is an object of the present invention to provide a fusion protein which is highly effective in the treatment and prevention of diseases caused by HPV.

It is another object of the present invention to provide a polynucleotide encoding the fusion protein.

It is a still another object of the present invention to provide a recombinant vector comprising the polynucleotide.

It is a still another object of the present invention to provide a pharmaceutical composition comprising the fusion protein and the recombinant vector.

It is a still another object of the present invention to provide a method for the treatment or prevention of diseases caused by HPV using the pharmaceutical composition in a subject.

BEST MODE

Figure 1:
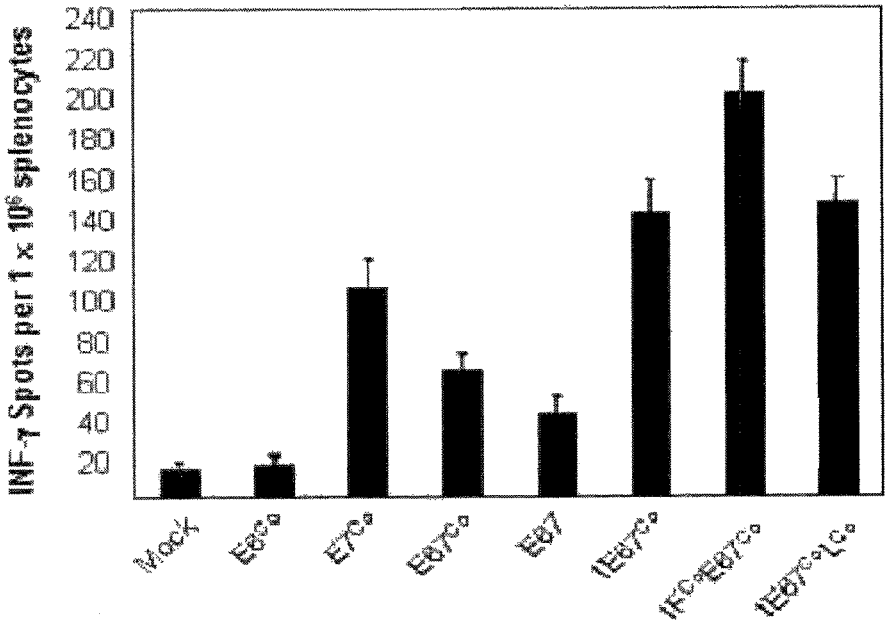
FIG. 1 is a graph illustrating the comparison results of the E7 specific $CD8^+$ T cell responses produced by vaccination of plasmid DNAs which express Mock, $E6^{Co}$, $E7^{Co}$, E67 and $E67^{Co}$, $tE67^{Co}$, $tF^{Co}E67^{Co}$ and $tE67^{Co}L^{Co}$ in a C57BL/6 mouse model.

According to an aspect of the present invention, there is provided a fusion protein comprising a fusion polypeptide of E6 and E7 of a human papilloma virus (HPV), a signal peptide for secreting the polypeptide out of the cell, and an immune enhancing peptide for a subject.

The E6 and E7 that constitute the fusion polypeptide of the present invention are antigen proteins derived from human papilloma virus (HPV) types 16, 18, 31, 33, 45 and 51, and they are preferably E6 and E7 antigen proteins derived from human papilloma virus types 16 (HPV16) or 18 (HPV18).

In the present invention, the expression "fusion polypeptide of E6 and E7 of a human papilloma virus" refers to a fusion protein of a polypeptide in which each of E6 and E7 has a natural amino acid sequence, or either of E6 and E7 has an amino acid mutant of a natural amino acid sequence. As used herein, the term "mutant" refers to a polypeptide, which has a different amino acid sequence from a natural amino acid sequence by subjecting at least one amino acid residue to deletion, insertion, conservative substitution, or a combination thereof, but has substantially the same immunogenicity as that of a natural E6 and E7 polypeptide, and can occur naturally or artificially. In one embodiment, the mutants may be exemplified by SEQ ID NO: 4, in which the 63rd and 106the cysteins are substituted with glycines in the amino acid sequence encoding E6 polypeptide of a human papilloma virus type 16 (HPV16); SEQ ID NO: 6, in which the 24th cysteine and the 26th glutamic acid are substituted with glycines in the amino acid sequence encoding E7 polypeptide of HPV16; SEQ ID NO: 10, in which the 65th and 108th cysteine are substituted with glycines in the amino acid sequence encoding E6 polypeptide of HPV18; or SEQ ID NO: 12, in which the 27th cysteine and the 29th glutamic acid are substituted with glycines in the amino acid sequence encoding E7 polypeptide of HPV18.

The fusion polypeptide of E6 and E7 of a human papilloma virus of the present invention may be in the form of an E6/E7 fusion polypeptide, in which E6 is at the amino terminal with respect to E7, that is, E6 is followed by E7 (E6/E7 fusion polypeptide); or in which E6 is at the carboxyl terminal with respect to E7, that is, E7 is followed by E6 (E7/E6 fusion polypeptide). In specific embodiments, the fusion polypeptide may be exemplified by the HPV16 E6/E7 fusion polypeptide of SEQ ID NO: 8, or the HPV18 E6/E7 fusion polypeptide of SEQ ID NO: 14.

In the present invention, the phase "signal peptide" refers to a peptide consisting of about 20 to 30 amino acids, which secrets a protein expressed within a cell, in particular, a protein comprising an E6/E7 fusion polypeptide, out of the cell. The signal peptide for secreting the polypeptide out of the cell, and a nucleic acid sequence encoding the same are referred to as a "secretory signal sequence". The E6 and E7 antigens of the present invention is a protein expressed within the nucleus of the cell which has been infected with a virus (a nucleus protein), and as a result, has weak immunity. Thus, the signal peptide expressed by the secretory signal sequence can induce the secretion of E6 and E7 antigens out of the cell to increase an antigen-specific humoral immune response, and a cellular immune response. Therefore, for the signal peptide of the present invention, secretory signal sequences, etc. of tPA, HSV gDs, and growth hormone can be used, but are not limited thereto. Preferably, a signal peptide used in higher eukaryotic cells including a mammal, more preferably tPA (tissue plasminogen activator) can be used.

As used herein, the phrase "immune enhancing peptide" refers to a peptide which activates cells associated with immune responses to increases the immune responses (e.g., dendritic cells, etc.). Examples of the immune enhancing peptides include a CD40 ligand, an Flt3 ligand, a Flagellin, and OX40. In the present invention, at least one immune enhancing peptide can be selected from the above-listed peptides to use, and preferably the peptide can be selected individually to use. In specific embodiments of the present invention, the CD40 ligand and the Flt3 ligand are used individually or in a combination thereof. The "Flt3 ligand" of the present invention is a factor which induces the proliferation and maturation of the dendritic cells (DC), which increase an immune response by an antigen, and is highly effective in reducing a tumor when fused with the tumor antigen. As used herein, the phrase "CD40 ligand" is a ligand which interacts with CD40 present on the surfaces of antigen presenting cells (APC) such as dendritic cells to activate the dendritic cells, etc.

As used herein, the "subject" encompasses mammals such as a human, a monkey, a mouse, a pig, a cow, and a rabbit, but is not limited thereto.

The fusion protein of the present invention is highly effective in antigen-specific immune responses, and in inhibition of occurrence and growth of a tumor. Indeed, a fusion polypeptide of E6 and E7 of a human papilloma virus induced both E6- and E7-specific $CD8^+$ T cell responses and showed stronger antitumor effect than did E6 or E7. In addition, it was found that a fusion protein, in which the fusion polypeptide of E6 and E7 of a human papilloma virus is bound with a signal peptide and an immune enhancing peptide, results in a highly effective antigen-specific immune response, and inhibits the occurrence and growth of a tumor. In specific embodiments, it was found that a fusion protein, in which the fusion polypeptide of E6 and E7 of a human papilloma virus is bound with tPa as a signal peptide, and a Flt3 ligand and/or a CD40 ligand as an immune enhancer is highly effective in an antigen-specific immune response, inhibition of occurrence and growth of a tumor, and inhibition of a tumor size, as compared with each of E6 and E7 of a human papilloma virus. Accordingly, the fusion protein of the present invention can be used for the treatment and prevention of a tumor.

Another embodiment of the present invention relates to a polynucleotide encoding the fusion protein.

The polynucleotide of the present invention can be prepared by a chemical synthesis method, or a genetic engineering technology. The chemical synthesis methods are known to a skilled person in the art, and any of the methods can be used. Further, it may be purchased from a commercial synthesizer or manufacturer. In the case where it is prepared by a genetic engineering technology, for example, nucleic acid fragments encoding commercially known fusion polypeptide of E6 and E7, signal peptide, and immune enhancing peptide, respectively, and linking the fragments to fit with the frames. A method for obtaining the nucleic acid fragments is known in the art, and a skilled person in the art can link them with an appropriate restriction enzyme. In specific embodiments of the present invention, a method for preparing a polynucleotide by chemical synthesis is disclosed.

Still another embodiment of the present invention relates to a recombinant vector comprising the polynucleotide.

As used herein, the term "vector" refers to a genetic construct comprising a foreign DNA, which had been inserted into a genome encoding a polypeptide. As used herein, the phrase "expression vector" refers to a vector, in which a nucleic acid sequence encoding a secretory signal sequence, a nucleic acid sequence encoding a fusion polypeptide of E6 and E7 of a human papilloma virus, and a nucleic acid sequence encoding an immune enhancing peptide, or the like, are inserted into a genome, and examples thereof include a plasmid vector, a cosmid vector, a bacteriophage, a yeast vector, and a virus vector, such as an adenovirus vector, a retrovirus vector, an adeno-associated virus vector.

As used herein, the phrase "secretory signal sequence" refers to a nucleic acid sequence encoding a peptide which secretes a tumor antigen expressed within a cell out of the cell and allows it to be recognized by immune cells, and examples thereof include such secretory signal sequences as tPA, HSV gDs, and a growth hormone. Preferably, a secretory signal sequence used in higher eukaryotic cells of a mammal, more preferably tPA (tissue plasminogen activator) can be used. Further, the secretory signal sequence of the present invention can be used after substituting with a codon having a high expression frequency in a host cell.

As used herein, the expression "nucleic acid sequence encoding the immune enhancing peptide" refers to a nucleic acid sequence encoding a peptide which increases an immune response by the activation of cells associated with immune responses (e.g., dendritic cells, etc.). Examples of the immune enhancing peptides include a CD40 ligand, an Flt3 ligand, a Flagellin, and OX40. In the present invention, at least one can be selected from these immune enhancing peptides to use, and preferably each of the peptides can be selected to use. In specific embodiments of the present invention, the CD40 ligand and the Flt3 ligand are used individually or in a combination thereof. The nucleic acid sequence encoding the immune enhancing peptide can be used after substituting with a codon having a high expression frequency in a host cell.

The polynucleotide contained in recombinant vector of the present invention can be substituted with a codon having a high expression frequency in a host cell. As used herein, the expression "substitution with a codon having a high expression frequency in a host cell", or "codon optimization" refers to substituting a codon having high preference in some hosts among the codons designating the amino acids upon transcription and translation of DNAs to a protein in a host cell, with a codon having a higher preference, and thus increasing the expression efficiency of the amino acid or protein, encoded by the nucleic acids. Herein, the term "host cell" encompasses a prokaryotic cell, or a eukaryotic cell, and the eukaryotic cells includes a lower eukaryotic cell such as a fungus and a yeast, as well as a higher eukaryotic cell such as a mammal.

The polynucleotide encoding the fusion polypeptide of E6 and E7 of a human papilloma virus, which is contained in the recombinant vector of the present invention, can be substituted with some of the nucleic acid sequences encoding E6 and E7 so as to avoid the generation of oncogenicity, in addition to the codon optimization.

For the fusion polypeptide of E6 and E7 of a human papilloma virus of the present invention, the expression of E6 and E7 into a fusion polypeptide to be used as an immunogen more effectively induces an antitumor effect, as compared with individual expression of E6 and E7 to be used as an immunogen. Further, the nucleic acid sequence encoding the fusion polypeptide of E6 and E7 substituted with a codon having a high expression frequency in a host cell more effectively induces an antigen-specific immune response, as compared with that unsubstituted. Further, even if there occurs a mutation such that some nucleic acid sequence of E6 and E7 is deleted to avoid oncogenicity, an immune response can be effectively induced. In specific embodiments, the nucleic acid sequences of the E6/E7 fusion polypeptide having fusion with the polypeptides of the codon-optimized and -mutated HPV16 E6 and E7, or HPV18 E6 and E7 is depicted in SEQ ID NOs: 7 and 13. Further, the co-expression of the E6/E7 fusion polypeptide, and a signal peptide by a secretory signal sequence, and an immune enhancing peptide increases the effectiveness of an antigen-specific immune response, and inhibits the size and occurrence of a tumor, as compared with the expression of the E6/E7 fusion polypeptide alone.

The recombinant vector of the present invention can comprise a nucleic acid encoding the fusion protein in the form adapted for expression of the nucleic acids encoding the fusion protein of the present invention in the host cell. That is, the recombinant vector of the present invention comprises at least one regulatory sequence to be used for expression, selected on the basis of the host cells, and the regulatory sequence is operatively linked with a nucleic acid sequence to be expressed. The expression "operatively linked with" refers to a nucleotide sequence being linked to the regulator sequence so as to be expressed (for example, in an in-vitro transcription/translation system, or in a host cell). The phrase "regulatory sequence" is intended to include a promoter, an enhancer, and other regulatory elements (e.g., polyadenylation signal). The regulatory sequence encompasses one directing a desired nucleic acid to be expressed constitutively, and one directing a desired nucleic acid to be expressed in a specific host cell only (e.g., tissue-specific regulatory sequence) in a number of host cells. It will be understood by a skilled person in the art that the design of the expression vector can vary depending on the factors such as selection of the host cells to be transformed, and levels of expression of a desired protein. The expression vector of the present invention can be introduced into a host cell to express the fusion protein.

The vector of the present invention can be prepared, for example, by a standard recombination DNA technology, and the standard recombination DNA technologies include, for example, ligation of a blunt end and a sticky end, treatment with a restriction enzyme to provide an appropriate end, removal of a phosphate group by treatment with an alkaline phosphatase to avoid a non-specific binding, and enzymatic bonding by a T4 DNA ligase. Each of DNAs which encode signal peptides, fusion polypeptides of E6 and E7 of a human papilloma virus, and immune enhancing peptides, which are obtained by a chemical synthesis method, or a genetic engineering technology can be recombined with a vector containing an appropriate regulatory sequence to provide the vector of the present invention. The vector containing the regulatory sequence can be commercially available, or prepared, and in the present invention, it was prepared using pGX10, which is a vector used to prepare a vaccine as disclosed in Korean Patent Application Publication No. 2003-47667.

Still another embodiment of the present invention relates to a recombinant vector comprising the nucleic acid sequence, which encodes the E6/E7 polynucleotide, of SEQ ID NO: 7, or SEQ ID NO: 13, having optimization of codons, and substitution of nucleic acids encoding some amino acids.

The recombinant vector comprising the nucleic acid sequence of SEQ ID NO: 7, or SEQ ID NO: 13 of the present invention can further comprise a secretory signal sequence, and an amino acid sequence encoding an immune enhancing peptide. Examples of the secretory signal sequence include the secretory signal sequences of tPA, HSV, gDs, and a growth hormone, preferably secretory signal sequences used in higher eukaryotes such as a mammal, and more preferably tPa (tissue plasminogen activator). Examples of the above-mentioned sequence encoding the immune enhancing peptide include amino acid sequences encoding a CD40 ligand, an Flt3 ligand, a Flagellin, and OX40. At least one immune enhancing peptide can be selected from the above-listed peptides to use, and preferably the peptide can be selected individually to use. In the specific embodiments of the present invention, the CD40 ligand and the Flt3 ligand are used individually or in a combination thereof. Further, the secretory signal sequence and the nucleic acid sequence encoding the immune enhancing peptide are preferably substituted with a codon having a high expression frequency in a host cell. In specific embodiments, tPa contains the nucleic acid sequence of SEQ ID NO: 1, the Flt3 ligand contains the nucleic acid sequence of SEQ ID NO: 15, and the CD40 ligand contains the nucleic acid sequence of SEQ ID NO: 17.

In another embodiment, the recombinant vector of the present invention can be used for production of the fusion protein of the present invention, as a vector for gene transfer for gene therapy, or as a pharmaceutically active ingredient to be administered to a subject as it is.

Still another embodiment of the present invention relates to a pharmaceutical composition for the treatment and prevention of a disease caused by a human papilloma virus in a subject, comprising the fusion protein of the present invention and a pharmaceutically acceptable carrier. In the present invention, examples of the subject include a mammal, such as a human, a monkey, and a mouse, but are not limited thereto. Examples of the diseases caused by the virus include cervical cancer, condyloma acuminata, and wart.

Examples of the pharmaceutically acceptable carrier used in the composition of the present invention include lactose, glucose, sucrose, sorbitol, mannitol, starch, gum acacia, alginate, gelatin, calcium phosphate, calcium silicate, cellulose, methyl cellulose, microcrystalline cellulose, polyvinylpyrrolidone, water, methylhydroxybenzoate, propylhydroxybenzoate, talc, magnesium stearate and mineral oil. The composition may additionally include a lubricant, a wetting agent, a flavoring agent, an emulsifier, a preservative, and the like.

The composition of the present invention can be administered to a subject by any of various routes including intravenous, intramuscular, oral, transdermal, transcutaneous, intranasal, intratracheal, and subcutaneous administrations, but not limited thereto. The composition of the present invention can be indirectly administered into a subject by administering the composition into a cell cultured in vitro, and then administering the cultured cell into a body of the subject. The composition of the present invention can be administered systematically or topically.

The composition of the present invention may be formulated into oral dosage forms including, but not limited to, granules, powders, solutions, tablets, capsules, dry syrup and the like, or parenteral dosage forms including injectables. The composition of the present invention is preferably in the dosage form of solutions or injectables.

The effective amount of the fusion protein of the present invention as the active ingredient may range from about 0.05 to 500 mg/kg body weight, preferably 0.5 to 50 mg/kg body weight, and can be administered in a single dose or in divided doses. However, it should be understood that the amount of the active ingredient administered should be determined in light of various relevant factors including the condition to be treated, the age and weight of a patient, and the severity of the patient's symptom; and, therefore, the above dose should not be construed to limit the scope of the invention in any way.

Still another embodiment of the present invention relates to a pharmaceutical composition for the treatment and prevention of a disease caused by a human papilloma virus in a subject, comprising the recombinant vector of the present invention and a pharmaceutically acceptable carrier. In the present invention, examples of the subject include a mammal, such as a human, a monkey, and a mouse, but are not limited thereto. Examples of the diseases caused by the virus include cervical cancer, condyloma acuminata, and wart.

Examples of the pharmaceutically acceptable carrier used in the composition of the present invention include lactose, dextrose, sucrose, sorbitol, mannitol, starch, gum acacia, alginate, gelatin, calcium phosphate, calcium silicate, cellulose, methyl cellulose, microcrystalline cellulose, polyvinylpyrrolidone, water, methylhydroxybenzoate, propylhydroxybenzoate, talc, magnesium stearate and mineral oil. The composition may additionally include a lubricant, a wetting agent, a flavoring agent, an emulsifier, a preservative, and the like.

The composition of the present invention can be administered to a subject by any of various routes including intravenous, intramuscular, oral, transdermal, transcutaneous, intranasal, intratracheal, and subcutaneous administrations, but not limited thereto. The composition of the present invention can be indirectly administered into a subject by administering the composition into a cell cultured in vitro, and then administering the cultured cell into a body of the subject. The composition of the present invention can be administered systematically or topically.

The composition of the present invention may be formulated into oral dosage forms including but not limited to, granules, powders, solutions, tablets, capsules, dry syrup and the like, or parenteral dosage forms including injectables. The composition of the present invention is preferably in the dosage form of solutions or injectables.

The effective amount of the fusion protein of the present invention as the active ingredient may range from about 0.05 to 500 mg/kg body weight, preferably 0.5 to 50 mg/kg body weight, and can be administered in a single dose or in divided doses. However, it should be understood that the amount of the active ingredient administered should be determined in light of various relevant factors including the condition to be treated, the age and weight of a patient, and the severity of the patient's symptom; and, therefore, the above dose should not be construed to limit the scope of the invention in any way.

Still another embodiment of the present invention relates to a method for the treatment of a disease caused by a human papilloma virus in a subject, comprising a step of administering a therapeutically effective amount of the pharmaceutical composition of the present invention to the subject.

The pharmaceutical composition of the present invention, the efficacy, administration mode and administration amount of the composition are as described above. In the method of the present invention, examples of the subject include a mammal, such as a human, a monkey, a mouse, a pig, a cow, and a rabbit, but are not limited thereto.

Hereinbelow, the present invention will be described with reference to Examples. However, Examples are provided only for the purpose of illustrating the present invention, and the scope of the present invention is not intended to be limited to Examples.

[Mode for Invention]

EXAMPLE 1

Construction of pGX10/tE67$^{Co}$ DNA

The abbreviations used in Examples of the present invention have the following definitions:

"Co" means a codon-optimized nucleic acid sequence; "tPa" or "t" means a secretory signal sequence of a tissue plasminogen activator; "F" means a Flt3 ligand; and a "L" means a CD40 ligand.

The codon-optimized tPa secretory signal sequence containing the nucleic acid sequence of SEQ ID NO: 1 was synthesized chemically. To the ends, EcoRI-KpnI (5') and Eco47III-NheI (3') sites were added. The codon-optimized HPV16E6E7 containing the nucleic acid sequence of SEQ ID NO: 7 was synthesized chemically, and to the ends, Eco47III-NheI (5') and AscI-XhoI (3') sites were added to facilitate insertion into the vector. Further, to the junction of E6 and E7, a BamHI site was added. In order to eliminate the property of causing oncogenicity, in E6, the 63rd codon (cystein) was substituted with glycine; and the 106th codon (cystein) was substituted with a codon designating glycine (SEQ ID NO: 3). In E7, the 24th codon (cystein) was substituted with glycine; and the 26th codon (glutamine) was substituted with a codon designating glycine (SEQ ID NO: 5). A vector for the preparation of a DNA vaccine, pGX10 (in Korean Patent Application Publication No. 2003-0047667), was treated with EcoRI and NheI enzymes to link with the synthesized secretory signal sequence, tPa, using a ligase. The resultant was cleaved using NheI and XhoI enzymes to link with HPV16E6E7 using a ligase, to prepare pGX10/tE67$^{Co}$.

EXAMPLE 2

Construction of pGX10/tF$^{Co}$E67$^{Co}$ DNA

The codon-optimized tPa secretory signal sequence containing the nucleic acid sequence of SEQ ID NO: 1, and the codon-optimized Flt3L containing the nucleic acid sequence of SEQ ID NO: 15 were synthesized chemically in the linked form. To the ends, KpnI (5') and EcoRV (3') sites were added to facilitate insertion into the vector. The pGX10/tE67$^{Co}$ prepared in Example 1 was treated with KpnI and Eco47III enzymes, and only the secretory signal sequence, tPa, was removed. Then, tF$^{Co}$ was linked using a ligase, to prepare pGX10/tF$^{Co}$E67$^{Co}$.

EXAMPLE 3

Construction of pGX10/tE67$^{Co}$L$^{Co}$ DNA

The codon-optimized CD40L containing the nucleic acid sequence of SEQ ID NO: 17 was synthesized chemically. To the ends, AscI (5'), and XhoI (3') sites were added to facilitate insertion into the vector. The pGX10/tE67$^{Co}$ prepared in Example 1 was treated with AscI and XhoI enzymes, and the CD40L$^{Co}$ was linked using a ligase, to prepare pGX10/tE67$^{Co}$L$^{Co}$.

EXAMPLE 4

Figure 2:
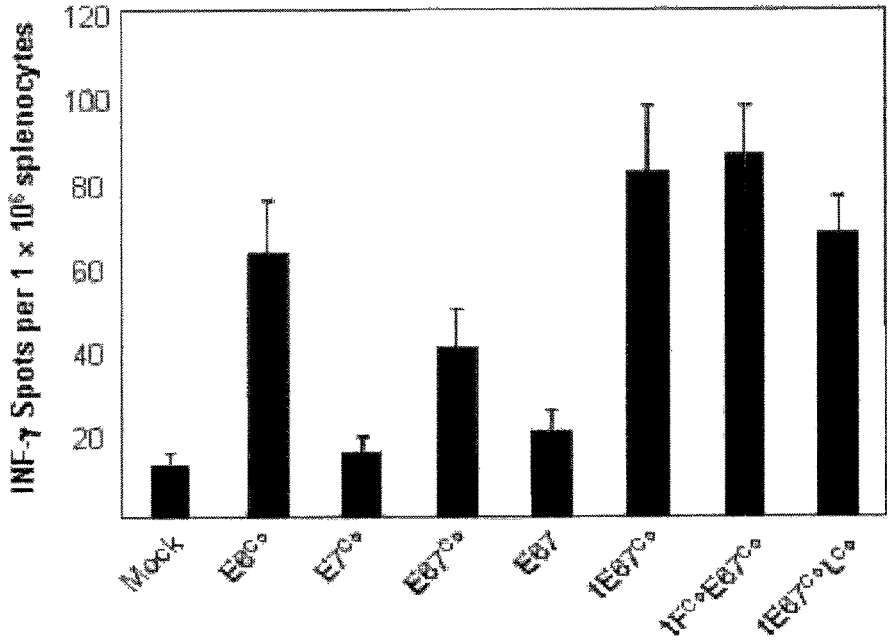
FIG. 2 is a graph illustrating the comparison results of the E6 specific $CD8^+$ T cell responses produced by vaccination of Mock, $E6^{Co}$, $E7^{Co}$, E67 and $E67^{Co}$, $tE67^{Co}$, $tF^{Co}E67^{Co}$ and $tE67^{Co}L^{Co}$ in a C57BL/6 mouse model.

Confirmation of Effects of Prevention of Cervical Cancer of pGX10/tE67$^{Co}$, pGX10/tF$^{Co}$E67$^{Co}$, and pGX10/tE67$^{Co}$L$^{Co}$ To confirm the effects of prevention of cervical cancer of pGX10/tE67$^{Co}$, pGX10/tF$^{Co}$E67$^{Co}$, and pGX10/tE67$^{Co}$L$^{Co}$, they were intramuscularly injected to a mouse C57BL/6, respectively, twice in an amount of 50 μg every fourth week, and pGX10, pGX10/E6$^{Co}$, pGX10/E7$^{Co}$, pGX10/E67$^{Co}$, and pGX10/E67 were intramuscularly injected to as the control groups in the same amount at the same interval. The spleen was taken out from the mouse at 6.5 weeks after initial intramuscular injection, and to a plate which had been coated with 50 μL of an anti-mouse IFN-γ antibody (BD Pharmingen, San Diego, Calif.) at 3 μg/ml, was put $1\times10^6$ cells, together with IL-2, and E6 or E7 CD8 T cell epitopes ($E6_{48-57}$; EVYD-FAFRDL, $E7_{49-57}$; RAHYNIVTF, Peptron, Korea). They were cultured in an incubator (Forma, Minn., USA) at 37° C. and 5% $CO_2$ for 24 hours. The plate was washed with PBST, and then 50 μL of an IFN-γ detecting antibody (BD Pharmingen, San Diego, Calif.) having a pendent biotin at 2 μg/mL was put thereto, and it was cultured at ambient temperature for about 3 hours. Thereafter, it was washed with PBST, and 50 μL of streptavidin-AKP (alkaline phosphate) which had been diluted to 1:2000 was added thereto, and the resultant was cultured at ambient temperature for 1 hour. It was washed with PBST, and then 50 μL of the mixture of 66 μL of NBT (Promega, Madison, WT) and 33 μL of BCIP (Promega, Madison, WT) in 10 mL of an alkaline phosphate buffer was added to the resultant to be reacted with each other. To obtain clear color expression by the reaction, the product was put into an incubator at 37° C. for about 30 min, and washed with distilled water (D. W), and the number of the generated spots was recorded by a reader (see FIGS. 1 and 2).

Using an E6 CD8 T cell epitope and an E7 CD8 T cell epitope, an E6/E7-specific T cell immune response was measured using ELISPOT, and as a result, it was found that pGX10/E67$^{Co}$ induced a higher degree of the antigen-specific immune response than pGX10/E67, indicating that codon-optimization is more effective for enhancing the antigen-specific immune response. Further, it was found that pGX10/tE67$^{Co}$ induced a higher degree of the CD8 T cell immune response than pGX10/E67$^{Co}$, indicating that the secretory signal sequence, tPa, is also effective for improving the antigen-specific immune response. Further, it was found that pGX10/tE67$^{Co}$L$^{Co}$ induced a lower degree of the E6 specific immune response than pGX10/tE67$^{Co}$, but induced substantially the same degree of the E7 specific response, as compared with the other control groups, indicating that it is effective for enhancing the immune response. It was confirmed that pGX10/tFE67$^{Co}$ is most effective for induction of the E6- and E7-specific immune response.

Figure 3:
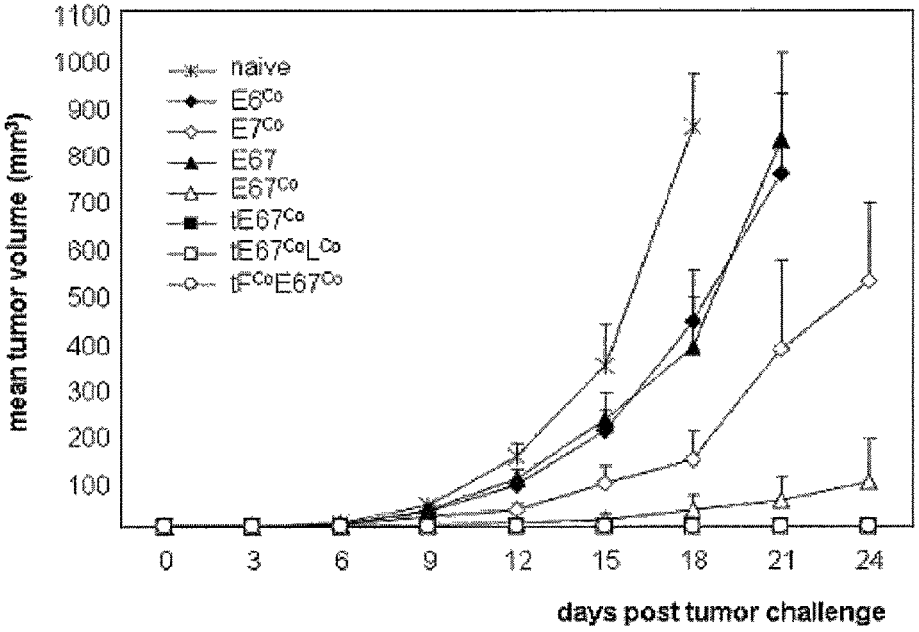
FIG. 3 is a graph illustrating the comparison results of the prophylactic antitumor effects against subcutaneous injection of TC-1 tumor cells, indicated by the increase in the volume of tumor mass, in vaccinated C57BL/6 mice with Mock, $E6^{Co}$, $E7^{Co}$, E67 and $E67^{Co}$, $tE67^{Co}$, $tF^{Co}E67^{Co}$ and $tE67^{Co}L^{Co}$.

At 6.5 weeks after initial injection, a tumor cell expressing the HPV16 E6 and E7, TC-1, was subcutaneously injected to a subject at $5\times10^5$ cells, and the increase in the volumes of the tumor cell was measured (see FIG. 3). Particularly, in the E6- and E7-specific immune response, the fusion product, E67$^{Co}$ induced a lower degree of the immune response, as compared with each of the E6$^{Co}$ and E7$^{Co}$ (see FIGS. 1 and 2), but showed a higher anti-cancer effect to the injected TC-1 tumor cell. This indicates that the E67 fusion product is better for the anti-cancer effect, since it can induce the immune responses against two tumor antigens, E6 and E7, simultaneously, rather than the individual immune response against one of them even though the response is strong. It was observed that tumor did not occur in the mouse which had been injected with pGX10/tE67$^{Co}$, pGX10/tF$^{Co}$E67$^{Co}$, and pGX10/tE67$^{Co}$L$^{Co}$ by day 24 after injection of a tumor cell, but the volume of a tumor was drastically increased in the other control group from the time point of day 9 after injection of a tumor cell. Therefore, it can be confirmed that pGX10/tE67$^{Co}$, pGX10/tF$^{Co}$E67$^{Co}$, and pGX10/tE67$^{Co}$L$^{Co}$ have higher ability of preventing cervical cancer.

EXAMPLE 5

Figure 4:
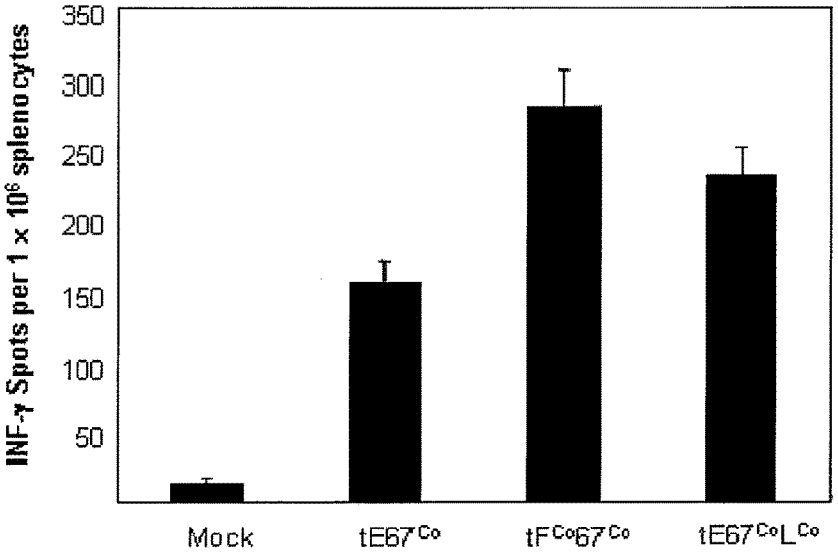
FIG. 4 is a graph illustrating the comparison results of the E7 specific $CD8^+$ T cell responses produced by treatment with mock, $tE67^{Co}$, $tF^{Co}E67^{Co}$ and $tE67^{Co}L^{Co}$ in a C57BL/6 mouse bearing TC-1 tumors.
Figure 5:
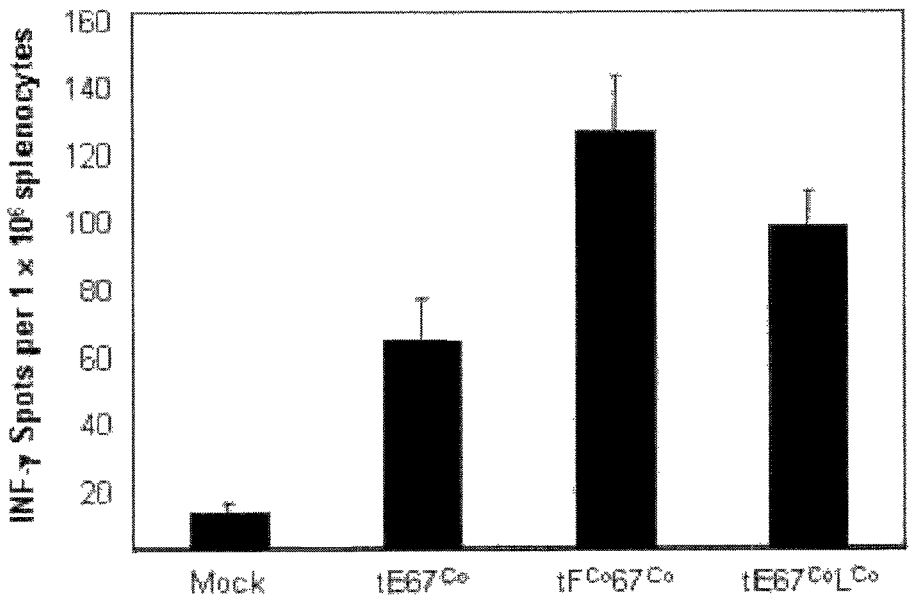
FIG. 5 is a graph illustrating the comparison results of the E6 specific $CD8^+$ T cell responses produced by treatment with mock, $tE67^{Co}$, $tF^{Co}E67^{Co}$ and $tE67^{Co}L^{Co}$ in a C57BL/6 mouse bearing TC-1 tumors.

Confirmation of Effects of Treatment of Cervical Cancer of pGX10/tE67$^{Co}$, pGX10/tF$^{Co}$E67$^{Co}$, pGX10/tE67$^{Co}$L$^{Co}$ To confirm the effects of treatment of cervical cancer of pGX10/tE67$^{Co}$, pGX10/tF$^{Co}$E67$^{Co}$, pGX10/tE67$^{Co}$L$^{Co}$, the TC-1 tumor cells were subcutaneously injected to a mouse C57BL/6 at $5\times10^5$ cells, respectively, and further muscularly injected in an amount of 50 μg at days 3, and 8 after initiating the injection of TC-1 tumor cells. Starting from the day when injection of the tumor cells (day 0), the change in the volumes of tumor mass was observed to day 21, and at day 22, the spleen was taken out from the mouse, and the degrees of induction of a CD8 T cell immune response which is specific to the antigens against E6 and E7 were measured in the same manner (ELISPOT) as described in Example 4. As compared with pGX10 as the control group, a higher degree of the antigen-specific immune response was induced in the mice treated with pGX10/tE67$^{Co}$, pGX10/tF$^{Co}$E67$^{Co}$, and pGX10/tE67$^{Co}$L$^{Co}$, and particularly a highest degree of the immune response was measured in the mouse treated with pGX10/tF$^{Co}$E67$^{Co}$, indicating that pGX10/tF$^{Co}$E67$^{Co}$ has a high efficacy of inducing an anti-cancer immune response (see FIGS. 4 and 5).

Figure 6:
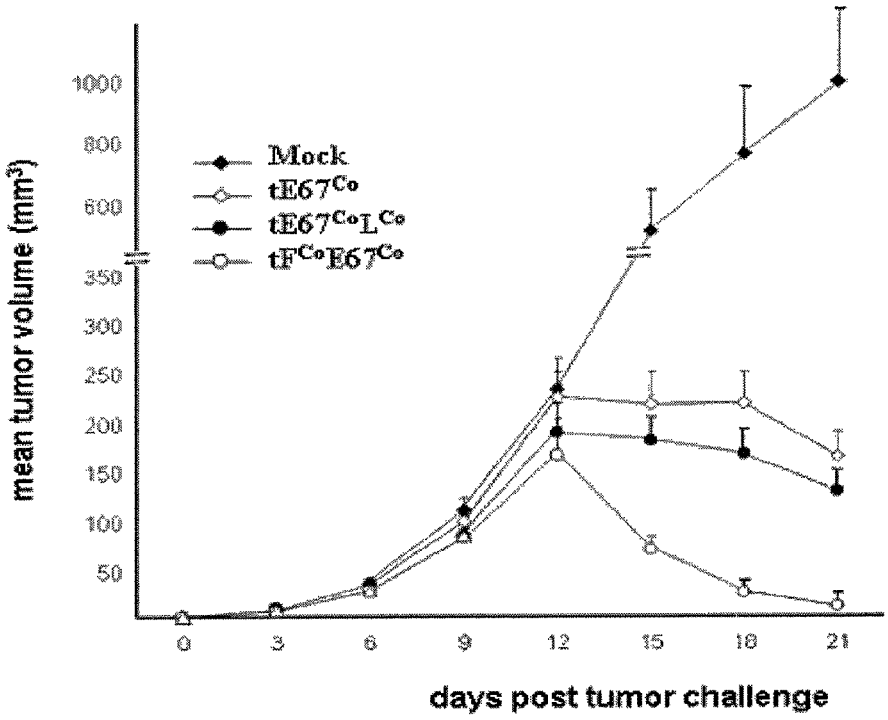
FIG. 6 is a graph illustrating the comparison results of the therapeutic antitumor effects produced by treatment with mock, $tE67^{Co}$, $tF^{Co}E67^{Co}$ and $tE67^{Co}L^{Co}$ in a C57BL/6 mouse bearing TC-1 tumor as a therapeutic model.

It was found that the mice which had been immune-treated with pGX10/tE67$^{Co}$, pGX10/tF$^{Co}$E67$^{Co}$, and pGX10/tE67$^{Co}$L$^{Co}$ against the TC-1 tumor cells showed significant reduction in the volume of a tumor, as compared with the mouse treated with pGX10, as the control group. Further, it was found that the volume of a tumor was continuously increased until day 12 after injection of the tumor cells, and then after that, the volume started to decrease, and particularly it was found that in the mice which had been immune-treated with pGX10/tF$^{Co}$E67$^{Co}$ and pGX10/tE67$^{Co}$L$^{Co}$, the volume of a tumor was substantially zero at day 21, indicating that it has an effect of treatment of cervical cancer (see FIG. 6).

---

SEQUENCE LISTING

```
<160> NUMBER OF SEQ ID NOS: 18

<210> SEQ ID NO 1
<211> LENGTH: 75
<212> TYPE: DNA
<213> ORGANISM: Artificial Sequence
<220> FEATURE:
<223> OTHER INFORMATION: codon optimized signal sequence of tissue
      plasminogen activator

<400> SEQUENCE: 1

atggacgcca tgaagcgcgg cctgtgctgc gtgctgctgc tgtgcggcgc cgtgtttgtg     60

agccccagcg ctagc                                                      75


<210> SEQ ID NO 2
<211> LENGTH: 25
<212> TYPE: PRT
<213> ORGANISM: Artificial Sequence
<220> FEATURE:
<223> OTHER INFORMATION: tissue plasminogen activator

<400> SEQUENCE: 2

Met Asp Ala Met Lys Arg Gly Leu Cys Cys Val Leu Leu Leu Cys Gly
1               5                   10                  15

Ala Val Phe Val Ser Pro Ser Ala Ser
            20                  25


<210> SEQ ID NO 3
<211> LENGTH: 477
<212> TYPE: DNA
<213> ORGANISM: Artificial Sequence
<220> FEATURE:
<223> OTHER INFORMATION: codon optimized and mutated HPV16 E6

<400> SEQUENCE: 3

atgcaccaga agcggaccgc tatgtttcag gaccctcagg aacggcctcg gaaactgcct     60

cagctgtgca ccgagctgca gaccaccatc cacgacatca tcctggagtg cgtgtactgc    120
```

```
aaacagcagc tgctccggcg ggaggtgtac gacttcgctt ttcgggatct gtgcatcgtg    180

taccgggacg gcaacccata tgctgtgggc gacaagtgtt taaagttcta cagcaagatc    240

agcgagtacc ggcactactg ctacagcctg tacggcacca ccctggagca gcagtacaac    300

aaacctctgt gcgacctgct catccggtgc atcaatggcc agaaacctct gtgccctgag    360

gaaaagcagc ggcacctgga caagaaacag cggtttcaca atatccgggg ccggtggacc    420

ggccggtgca tgagctgctg ccggagcagc cggacccggc gggaaaccca gctgtga       477


<210> SEQ ID NO 4
<211> LENGTH: 158
<212> TYPE: PRT
<213> ORGANISM: Artificial Sequence
<220> FEATURE:
<223> OTHER INFORMATION: HPV16 E6

<400> SEQUENCE: 4

Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
            20                  25                  30

Ile Ile Leu Glu Cys Val Tyr Cys Lys Gln Gln Leu Leu Arg Arg Glu
        35                  40                  45

Val Tyr Asp Phe Ala Phe Arg Asp Leu Cys Ile Val Tyr Arg Asp Gly
    50                  55                  60

Asn Pro Tyr Ala Val Gly Asp Lys Cys Leu Lys Phe Tyr Ser Lys Ile
65                  70                  75                  80

Ser Glu Tyr Arg His Tyr Cys Tyr Ser Leu Tyr Gly Thr Thr Leu Glu
                85                  90                  95

Gln Gln Tyr Asn Lys Pro Leu Cys Asp Leu Leu Ile Arg Cys Ile Asn
            100                 105                 110

Gly Gln Lys Pro Leu Cys Pro Glu Glu Lys Gln Arg His Leu Asp Lys
        115                 120                 125

Lys Gln Arg Phe His Asn Ile Arg Gly Arg Trp Thr Gly Arg Cys Met
    130                 135                 140

Ser Cys Cys Arg Ser Ser Arg Thr Arg Arg Glu Thr Gln Leu
145                 150                 155


<210> SEQ ID NO 5
<211> LENGTH: 297
<212> TYPE: DNA
<213> ORGANISM: Artificial Sequence
<220> FEATURE:
<223> OTHER INFORMATION: codon optimized and mutated HPV16 E7

<400> SEQUENCE: 5

atgcacggcg ataccccccac cctgcacgag tacatgctgg atctgcagcc tgaaaccacc     60

gatctgtacg gctacggcca gctgaacgac agctccgagg aagaagatga aatcgatggc    120

cctgctggcc aggctgaacc tgaccgggcc cactacaaca tcgtgacctt ctgctgcaaa    180

tgcgatagca ccctgcggct gtgcgtgcag agcacccacg tagacatccg gaccctggag    240

gatctgctca tgggcaccct gggcatcgtg tgccctatct gcagccagaa accttga       297


<210> SEQ ID NO 6
<211> LENGTH: 98
<212> TYPE: PRT
<213> ORGANISM: Artificial Sequence
<220> FEATURE:
<223> OTHER INFORMATION: HPV16 E7
```

<400> SEQUENCE: 6

Met His Gly Asp Thr Pro Thr Leu His Glu Tyr Met Leu Asp Leu Gln
1 5 10 15

Pro Glu Thr Thr Asp Leu Tyr Gly Tyr Gly Gln Leu Asn Asp Ser Ser
20 25 30

Glu Glu Glu Asp Glu Ile Asp Gly Pro Ala Gly Gln Ala Glu Pro Asp
35 40 45

Arg Ala His Tyr Asn Ile Val Thr Phe Cys Cys Lys Cys Asp Ser Thr
50 55 60

Leu Arg Leu Cys Val Gln Ser Thr His Val Asp Ile Arg Thr Leu Glu
65 70 75 80

Asp Leu Leu Met Gly Thr Leu Gly Ile Val Cys Pro Ile Cys Ser Gln
85 90 95

Lys Pro

<210> SEQ ID NO 7
<211> LENGTH: 789
<212> TYPE: DNA
<213> ORGANISM: Artificial Sequence
<220> FEATURE:
<223> OTHER INFORMATION: codon optimized and mutated HPV16 E6E7

<400> SEQUENCE: 7 atgcaccaga agcggaccgc tatgtttcag gaccctcagg aacggcctcg gaaactgcct 60 cagctgtgca ccgagctgca gaccaccatc cacgacatca tcctggagtg cgtgtactgc 120 aaacagcagc tgctccggcg ggaggtgtac gacttcgctt ttcgggatct gtgcatcgtg 180 taccgggacg gcaacccata tgctgtgggc gacaagtgtt taaagttcta cagcaagatc 240 agcgagtacc ggcactactg ctacagcctg tacggcacca ccctggagca gcagtacaac 300 aaacctctgt gcgacctgct catccggtgc atcaatggcc agaaacctct gtgccctgag 360 gaaaagcagc ggcacctgga caagaaacag cggtttcaca atatccgggg ccggtggacc 420 ggccggtgca tgagctgctg ccggagcagc cggacccggc gggaaaccca gctgggaagc 480 ggatccggca gcatgcacgg cgataccccc accctgcacg agtacatgct ggatctgcag 540 cctgaaacca ccgatctgta cggctacggc cagctgaacg acagctccga ggaagaagat 600 gaaatcgatg gccctgctgg ccaggctgaa cctgaccggg cccactacaa catcgtgacc 660 ttctgctgca aatgcgatag caccctgcgg ctgtgcgtgc agagcaccca cgtagacatc 720 cggaccctgg aggatctgct catgggcacc ctgggcatcg tgtgccctat ctgcagccag 780 aaaccttga 789

<210> SEQ ID NO 8
<211> LENGTH: 262
<212> TYPE: PRT
<213> ORGANISM: Artificial Sequence
<220> FEATURE:
<223> OTHER INFORMATION: HPV16 E6E7

<400> SEQUENCE: 8

Met His Gln Lys Arg Thr Ala Met Phe Gln Asp Pro Gln Glu Arg Pro
1 5 10 15

Arg Lys Leu Pro Gln Leu Cys Thr Glu Leu Gln Thr Thr Ile His Asp
20 25 30

Ile Ile Leu Glu Cys Val Tyr Cys Lys Gln Gln Leu Leu Arg Arg Glu
35 40 45

```
Val Tyr Asp Phe Ala Phe Arg Asp Leu Cys Ile Val Tyr Arg Asp Gly
    50                  55                  60

Asn Pro Tyr Ala Val Gly Asp Lys Cys Leu Lys Phe Tyr Ser Lys Ile
65                  70                  75                  80

Ser Glu Tyr Arg His Tyr Cys Tyr Ser Leu Tyr Gly Thr Thr Leu Glu
                85                  90                  95

Gln Gln Tyr Asn Lys Pro Leu Cys Asp Leu Leu Ile Arg Cys Ile Asn
            100                 105                 110

Gly Gln Lys Pro Leu Cys Pro Glu Glu Lys Gln Arg His Leu Asp Lys
        115                 120                 125

Lys Gln Arg Phe His Asn Ile Arg Gly Arg Trp Thr Gly Arg Cys Met
    130                 135                 140

Ser Cys Cys Arg Ser Ser Arg Thr Arg Arg Glu Thr Gln Leu Gly Ser
145                 150                 155                 160

Gly Ser Gly Ser Met His Gly Asp Thr Pro Thr Leu His Glu Tyr Met
                165                 170                 175

Leu Asp Leu Gln Pro Glu Thr Thr Asp Leu Tyr Gly Tyr Gly Gln Leu
            180                 185                 190

Asn Asp Ser Ser Glu Glu Glu Asp Glu Ile Asp Gly Pro Ala Gly Gln
        195                 200                 205

Ala Glu Pro Asp Arg Ala His Tyr Asn Ile Val Thr Phe Cys Cys Lys
    210                 215                 220

Cys Asp Ser Thr Leu Arg Leu Cys Val Gln Ser Thr His Val Asp Ile
225                 230                 235                 240

Arg Thr Leu Glu Asp Leu Leu Met Gly Thr Leu Gly Ile Val Cys Pro
                245                 250                 255

Ile Cys Ser Gln Lys Pro
            260


<210> SEQ ID NO 9
<211> LENGTH: 555
<212> TYPE: DNA
<213> ORGANISM: Artificial Sequence
<220> FEATURE:
<223> OTHER INFORMATION: codon optimized and mutated HPV18 E6

<400> SEQUENCE: 9

atggacgcca tgaagagggg cctgtgctgc gtgctgctgc tgtgcggcgc cgtgttcgtg      60

agccccagcg ctagcgctat ggcgcgcttt gaggatccaa cacggcgacc ctacaagcta     120

cctgatctgt gcacggaact gaacacttca ctgcaagaca tagaaataac ctgtgtatat     180

tgcaagacag tattggaact tacagaggta tttgaatttg catttaaaga tttatttgtg     240

gtgtatagag acagtatacc gcatgctgca ggccataaat gtatagattt ttattctaga     300

attagagaat taagacatta ttcagactct gtgtatggag acacattgga aaaactaact     360

aacactgggt tatacaattt attaataagg tgcctgcggg gtcagaaacc gttgaatcca     420

gcagaaaaac ttagacacct taatgaaaaa cgacgatttc acaacatagc tgggcactat     480

agaggccagt gccattcgtg ctgcaaccga gcacgacagg aaagactcca acgacgcaga     540

gaaacacaag tatga                                                      555


<210> SEQ ID NO 10
<211> LENGTH: 184
<212> TYPE: PRT
<213> ORGANISM: Artificial Sequence
<220> FEATURE:
```

<223> OTHER INFORMATION: HPV18 E6

<400> SEQUENCE: 10

Met Asp Ala Met Lys Arg Gly Leu Cys Cys Val Leu Leu Leu Cys Gly
1 5 10 15

Ala Val Phe Val Ser Pro Ser Ala Ser Ala Met Ala Arg Phe Glu Asp
20 25 30

Pro Thr Arg Arg Pro Tyr Lys Leu Pro Asp Leu Cys Thr Glu Leu Asn
35 40 45

Thr Ser Leu Gln Asp Ile Glu Ile Thr Cys Val Tyr Cys Lys Thr Val
50 55 60

Leu Glu Leu Thr Glu Val Phe Glu Phe Ala Phe Lys Asp Leu Phe Val
65 70 75 80

Val Tyr Arg Asp Ser Ile Pro His Ala Ala Gly His Lys Cys Ile Asp
85 90 95

Phe Tyr Ser Arg Ile Arg Glu Leu Arg His Tyr Ser Asp Ser Val Tyr
100 105 110

Gly Asp Thr Leu Glu Lys Leu Thr Asn Thr Gly Leu Tyr Asn Leu Leu
115 120 125

Ile Arg Cys Leu Arg Gly Gln Lys Pro Leu Asn Pro Ala Glu Lys Leu
130 135 140

Arg His Leu Asn Glu Lys Arg Arg Phe His Asn Ile Ala Gly His Tyr
145 150 155 160

Arg Gly Gln Cys His Ser Cys Cys Asn Arg Ala Arg Gln Glu Arg Leu
165 170 175

Gln Arg Arg Arg Glu Thr Gln Val
180

<210> SEQ ID NO 11
<211> LENGTH: 318
<212> TYPE: DNA
<213> ORGANISM: Artificial Sequence
<220> FEATURE:
<223> OTHER INFORMATION: codon optimized and mutated HPV18 E7

<400> SEQUENCE: 11 atgcatggac ctaaggcaac attgcaagac attgtattgc atttagagcc ccaaaatgaa 60 attccggttg accttctagg tcacgggcaa ttaagcgact cagaggaaga aaacgatgaa 120 atagatggag ttaatcatca acatttacca gcccgacgag ctgaaccaca acgtcacaca 180 atgttgtgta tgtgttgtaa gtgtgaagcc agaattgagc tagtagtaga aagctcagca 240 gacgaccttc gagcattcca gcagctgttt ctgaacaccc tgtcctttgt gtgtccgtgg 300 tgtgcatccc agcagtaa 318

<210> SEQ ID NO 12
<211> LENGTH: 105
<212> TYPE: PRT
<213> ORGANISM: Artificial Sequence
<220> FEATURE:
<223> OTHER INFORMATION: HPV18 E7

<400> SEQUENCE: 12

Met His Gly Pro Lys Ala Thr Leu Gln Asp Ile Val Leu His Leu Glu
1 5 10 15

Pro Gln Asn Glu Ile Pro Val Asp Leu Leu Gly His Gly Gln Leu Ser
20 25 30

Asp Ser Glu Glu Glu Asn Asp Glu Ile Asp Gly Val Asn His Gln His

```
        35                  40                  45

Leu Pro Ala Arg Arg Ala Glu Pro Gln Arg His Thr Met Leu Cys Met
    50                  55                  60

Cys Cys Lys Cys Glu Ala Arg Ile Glu Leu Val Val Glu Ser Ser Ala
65                  70                  75                  80

Asp Asp Leu Arg Ala Phe Gln Gln Leu Phe Leu Asn Thr Leu Ser Phe
                85                  90                  95

Val Cys Pro Trp Cys Ala Ser Gln Gln
            100                 105


<210> SEQ ID NO 13
<211> LENGTH: 888
<212> TYPE: DNA
<213> ORGANISM: Artificial Sequence
<220> FEATURE:
<223> OTHER INFORMATION: codon optimized  and mutated HPV18 E6E7

<400> SEQUENCE: 13

atggacgcca tgaagagggg cctgtgctgc gtgctgctgc tgtgcggcgc cgtgttcgtg     60

agccccagcg ctagcgctat ggcgcgcttt gaggatccaa cacggcgacc ctacaagcta    120

cctgatctgt gcacggaact gaacacttca ctgcaagaca tagaaataac ctgtgtatat    180

tgcaagacag tattggaact tacagaggta tttgaatttg catttaaaga tttatttgtg    240

gtgtatagag acagtatacc gcatgctgca ggccataaat gtatagattt ttattctaga    300

attagagaat taagacatta ttcagactct gtgtatggag acacattgga aaaactaact    360

aacactgggt tatacaattt attaataagg tgcctgcggg gtcagaaacc gttgaatcca    420

gcagaaaaac ttagacacct taatgaaaaa cgacgatttc acaacatagc tgggcactat    480

agaggccagt gccattcgtg ctgcaaccga gcacgacagg aaagactcca acgacgcaga    540

gaaacacaag taggatctgg atccggctcc atgcatggac ctaaggcaac attgcaagac    600

attgtattgc atttagagcc ccaaaatgaa attccggttg accttctagg tcacgggcaa    660

ttaagcgact cagaggaaga aaacgatgaa atagatggag ttaatcatca acatttacca    720

gcccgacgag ctgaaccaca acgtcacaca atgttgtgta tgtgttgtaa gtgtgaagcc    780

agaattgagc tagtagtaga aagctcagca gacgaccttc gagcattcca gcagctgttt    840

ctgaacaccc tgtcctttgt gtgtccgtgg tgtgcatccc agcagtaa                 888


<210> SEQ ID NO 14
<211> LENGTH: 295
<212> TYPE: PRT
<213> ORGANISM: Artificial Sequence
<220> FEATURE:
<223> OTHER INFORMATION: HPV18 E6E7

<400> SEQUENCE: 14

Met Asp Ala Met Lys Arg Gly Leu Cys Cys Val Leu Leu Leu Cys Gly
1               5                   10                  15

Ala Val Phe Val Ser Pro Ser Ala Ser Ala Met Ala Arg Phe Glu Asp
            20                  25                  30

Pro Thr Arg Arg Pro Tyr Lys Leu Pro Asp Leu Cys Thr Glu Leu Asn
        35                  40                  45

Thr Ser Leu Gln Asp Ile Glu Ile Thr Cys Val Tyr Cys Lys Thr Val
    50                  55                  60

Leu Glu Leu Thr Glu Val Phe Glu Phe Ala Phe Lys Asp Leu Phe Val
65                  70                  75                  80
```

```
Val Tyr Arg Asp Ser Ile Pro His Ala Ala Gly His Lys Cys Ile Asp
                85                  90                  95

Phe Tyr Ser Arg Ile Arg Glu Leu Arg His Tyr Ser Asp Ser Val Tyr
            100                 105                 110

Gly Asp Thr Leu Glu Lys Leu Thr Asn Thr Gly Leu Tyr Asn Leu Leu
        115                 120                 125

Ile Arg Cys Leu Arg Gly Gln Lys Pro Leu Asn Pro Ala Glu Lys Leu
    130                 135                 140

Arg His Leu Asn Glu Lys Arg Arg Phe His Asn Ile Ala Gly His Tyr
145                 150                 155                 160

Arg Gly Gln Cys His Ser Cys Cys Asn Arg Ala Arg Gln Glu Arg Leu
                165                 170                 175

Gln Arg Arg Arg Glu Thr Gln Val Gly Ser Gly Ser Gly Ser Met His
            180                 185                 190

Gly Pro Lys Ala Thr Leu Gln Asp Ile Val Leu His Leu Glu Pro Gln
        195                 200                 205

Asn Glu Ile Pro Val Asp Leu Leu Gly His Gly Gln Leu Ser Asp Ser
    210                 215                 220

Glu Glu Glu Asn Asp Glu Ile Asp Gly Val Asn His Gln His Leu Pro
225                 230                 235                 240

Ala Arg Arg Ala Glu Pro Gln Arg His Thr Met Leu Cys Met Cys Cys
                245                 250                 255

Lys Cys Glu Ala Arg Ile Glu Leu Val Val Glu Ser Ser Ala Asp Asp
            260                 265                 270

Leu Arg Ala Phe Gln Gln Leu Phe Leu Asn Thr Leu Ser Phe Val Cys
        275                 280                 285

Pro Trp Cys Ala Ser Gln Gln
    290                 295


<210> SEQ ID NO 15
<211> LENGTH: 474
<212> TYPE: DNA
<213> ORGANISM: Artificial Sequence
<220> FEATURE:
<223> OTHER INFORMATION: codon optimized Flt3L

<400> SEQUENCE: 15

atgacccagg actgcagctt ccagcacagc cccattagca gcgacttcgc cgtgaagatt     60

cgcgagctga gcgactacct gctgcaggac taccccgtga ccgtggccag caacctgcag    120

gacgaggagc tgtgcggcgg cctgtggcgc ctggtgctgg cccagcggtg gatggagcgc    180

ctgaagaccg tggccggcag caagatgcag ggcctgctgg agcgcgtgaa caccgagatt    240

cacttcgtga ccaagtgcgc cttccagccc ccccccagct gcctgcgctt cgtgcagacc    300

aacattagcc gcctgctgca ggagaccagc gagcagctgg tggccctgaa gccctggatt    360

acccgccaga acttcagccg ctgcctggag ctgcagtgcc agcccgacag cagcaccctg    420

cccccccct ggagcccccg ccccctggag gccaccgccc ccaccgcccc ctag          474


<210> SEQ ID NO 16
<211> LENGTH: 157
<212> TYPE: PRT
<213> ORGANISM: Artificial Sequence
<220> FEATURE:
<223> OTHER INFORMATION: Flt3L

<400> SEQUENCE: 16

Met Thr Gln Asp Cys Ser Phe Gln His Ser Pro Ile Ser Ser Asp Phe
```

```
1               5                   10                  15

Ala Val Lys Ile Arg Glu Leu Ser Asp Tyr Leu Leu Gln Asp Tyr Pro
            20                  25                  30

Val Thr Val Ala Ser Asn Leu Gln Asp Glu Glu Leu Cys Gly Gly Leu
        35                  40                  45

Trp Arg Leu Val Leu Ala Gln Arg Trp Met Glu Arg Leu Lys Thr Val
    50                  55                  60

Ala Gly Ser Lys Met Gln Gly Leu Leu Glu Arg Val Asn Thr Glu Ile
65                  70                  75                  80

His Phe Val Thr Lys Cys Ala Phe Gln Pro Pro Pro Ser Cys Leu Arg
                85                  90                  95

Phe Val Gln Thr Asn Ile Ser Arg Leu Leu Gln Glu Thr Ser Glu Gln
            100                 105                 110

Leu Val Ala Leu Lys Pro Trp Ile Thr Arg Gln Asn Phe Ser Arg Cys
        115                 120                 125

Leu Glu Leu Gln Cys Gln Pro Asp Ser Ser Thr Leu Pro Pro Pro Trp
    130                 135                 140

Ser Pro Arg Pro Leu Glu Ala Thr Ala Pro Thr Ala Pro
145                 150                 155


<210> SEQ ID NO 17
<211> LENGTH: 732
<212> TYPE: DNA
<213> ORGANISM: Artificial Sequence
<220> FEATURE:
<223> OTHER INFORMATION: codon optimized CD40L

<400> SEQUENCE: 17

atggacgcca tgaagcgcgg cctgtgctgc gtgctgctgc tgtgcggcgc cgtgttcgtg     60

agccccagcc gggcgaatga tgcgcaagcg ccgaaatcca aaatcgagga cgagcgcaac    120

ctgcacgagg acttcgtgtt tatgaagacc atccaacgct gtaataccgg cgagcgcagc    180

ctgagcctgc tcaattgcga agaaatcaag tcccaattcg aggggttcgt caaagacatc    240

atgctgaata aggaagaaac caagaaggag aactccttcg agatgcagaa gggcgaccaa    300

aacccccaga tcgccgccca cgtgatcagc gaagcgtcca gcaagaccac cagcgtcctg    360

caatgggccg agaagggcta ttatacgatg tccaataatc tggtgacgct cgagaacggc    420

aagcaactca cggtgaagcg ccagggcctg tactacattt acgcgcaggt gacgttttgc    480

agcaaccgcg aggccagcag ccaggccccc ttcatcgcgt ccctgtgtct gaaaagcccg    540

ggccgctttg aacgcattct gctgcgcgcc gccaacacgc atagcagcgc gaagccctgc    600

ggccagcaga gcatccatct gggcggcgtg ttcgagctgc agcccggcgc cagcgtcttc    660

gtcaacgtga ccgacccctc ccaggtctcc cacgggaccg ggtttaccag cttcgggctg    720

ctgaagctgt ga                                                        732


<210> SEQ ID NO 18
<211> LENGTH: 243
<212> TYPE: PRT
<213> ORGANISM: Artificial Sequence
<220> FEATURE:
<223> OTHER INFORMATION: CD40L

<400> SEQUENCE: 18

Met Asp Ala Met Lys Arg Gly Leu Cys Cys Val Leu Leu Leu Cys Gly
1               5                   10                  15

Ala Val Phe Val Ser Pro Ser Arg Ala Asn Asp Ala Gln Ala Pro Lys
```

-continued

```
            20                  25                  30

Ser Lys Ile Glu Asp Glu Arg Asn Leu His Glu Asp Phe Val Phe Met
        35                  40                  45

Lys Thr Ile Gln Arg Cys Asn Thr Gly Glu Arg Ser Leu Ser Leu Leu
    50                  55                  60

Asn Cys Glu Glu Ile Lys Ser Gln Phe Glu Gly Phe Val Lys Asp Ile
65                  70                  75                  80

Met Leu Asn Lys Glu Glu Thr Lys Lys Glu Asn Ser Phe Glu Met Gln
                85                  90                  95

Lys Gly Asp Gln Asn Pro Gln Ile Ala Ala His Val Ile Ser Glu Ala
            100                 105                 110

Ser Ser Lys Thr Thr Ser Val Leu Gln Trp Ala Glu Lys Gly Tyr Tyr
        115                 120                 125

Thr Met Ser Asn Asn Leu Val Thr Leu Glu Asn Gly Lys Gln Leu Thr
    130                 135                 140

Val Lys Arg Gln Gly Leu Tyr Tyr Ile Tyr Ala Gln Val Thr Phe Cys
145                 150                 155                 160

Ser Asn Arg Glu Ala Ser Ser Gln Ala Pro Phe Ile Ala Ser Leu Cys
                165                 170                 175

Leu Lys Ser Pro Gly Arg Phe Glu Arg Ile Leu Leu Arg Ala Ala Asn
            180                 185                 190

Thr His Ser Ser Ala Lys Pro Cys Gly Gln Gln Ser Ile His Leu Gly
        195                 200                 205

Gly Val Phe Glu Leu Gln Pro Gly Ala Ser Val Phe Val Asn Val Thr
    210                 215                 220

Asp Pro Ser Gln Val Ser His Gly Thr Gly Phe Thr Ser Phe Gly Leu
225                 230                 235                 240

Leu Lys Leu
```

The invention claimed is:

1. A fusion protein comprising a fusion polypeptide of E6 and E7 of a human papilloma virus type 16 (HPV16), a signal peptide tPa (tissue plasminogen activator), and an immune enhancing peptide Flt3 (fms-like tyrosine kinase receptor-3) ligand for a subject, wherein the fusion polypeptide of E6 and E7 has the amino acid sequence of SEQ ID NO: 8 or SEQ ID NO: 14.

2. The fusion protein according to claim 1, wherein tPa has the amino acid sequence of SEQ ID NO: 2.

3. The fusion protein according to claim 1, wherein the Flt3 ligand has the amino acid sequence of SEQ ID NO: 16.

4. A pharmaceutical composition for the treatment and prevention of a disease caused by a human papilloma virus in a subject, comprising the fusion protein of claim 1 and a pharmaceutically acceptable carrier.

* * * * *